(12) United States Patent
Derrick

(10) Patent No.: US 9,867,554 B2
(45) Date of Patent: Jan. 16, 2018

(54) ORAL/NASAL CANNULA MANIFOLD

(71) Applicant: Steven J. Derrick, West Mifflin, PA (US)

(72) Inventor: Steven J. Derrick, West Mifflin, PA (US)

(*) Notice: Subject to any disclaimer, the term of this patent is extended or adjusted under 35 U.S.C. 154(b) by 274 days.

(21) Appl. No.: 14/797,252

(22) Filed: Jul. 13, 2015

(65) Prior Publication Data
US 2017/0014047 A1 Jan. 19, 2017

(51) Int. Cl.
*A61B 5/08* (2006.01)
*A61B 5/097* (2006.01)
*A61M 16/06* (2006.01)
*A61M 16/08* (2006.01)
*A61B 5/00* (2006.01)
*A61M 16/10* (2006.01)
*A61B 5/083* (2006.01)

(52) U.S. Cl.
CPC .............. *A61B 5/097* (2013.01); *A61B 5/082* (2013.01); *A61B 5/0836* (2013.01); *A61B 5/4821* (2013.01); *A61M 16/0666* (2013.01); *A61M 16/0672* (2014.02); *A61M 16/085* (2014.02); *A61M 16/1005* (2014.02); *A61B 2560/04* (2013.01); *A61M 2230/432* (2013.01)

(58) Field of Classification Search
CPC ....................................................... A61B 5/097
See application file for complete search history.

(56) References Cited

U.S. PATENT DOCUMENTS

| | | | |
|---|---|---|---|
| 2007/0272247 A1* | 11/2007 | Porat ................. | A61M 16/0666 128/206.28 |
| 2014/0005565 A1* | 1/2014 | Derrick ................. | A61B 5/097 600/532 |

* cited by examiner

*Primary Examiner* — Christian Jang
(74) *Attorney, Agent, or Firm* — Carothers & Carothers

(57) ABSTRACT

An oral/nasal cannula manifold gas sampling and oxygen delivering manifold for sampling exhaled breath of a subject and delivering supplemental oxygen, the cannula including a main body portion having a suction port which is connected with a collection tube to a suction device for sampling the exhaled breath of the subject. A nasal prong upwardly protrudes from the main body portion and is positioned for insertion into a nostril of the subject to collect nasally exhaled breath. An oral conduit passage is embedded in a deflector/concentrator plate that extends downwardly from the main body portion and is also provided with a passage with an elongate lateral opening positioned for placement near the mouth of the subject to collect orally exhaled breath of the subject. The conduit passages of the nasal and oral passages are connected to and aligned in the same plane whereby the opposed nasal and oral conduit passages are connected with the conduit passage of the suction port without any adjacent connected void volumes or dead spaces in any of the passages.

3 Claims, 4 Drawing Sheets

ORAL/NASAL CANNULA MANIFOLD

CROSS REFERENCE

This application is a continuation-in-part of U.S. patent application Ser. No. 13/537,380, filed on 29 Jun. 2012, and entitled ORAL/NASAL CANNULA MANIFOLD.

FIELD OF THE INVENTION

The present invention relates to the field of oral/nasal cannula manifolds for use in sampling breath of subjects, especially for the purpose of providing capnographic data concerning the subject.

BACKGROUND OF THE INVENTION

During anesthesia, and especially during sedation anesthesia or patient controlled analgesia it is often desirable to collect and analyze qualitatively and quantitatively the constituents of gases respired by the patient.

Oral/nasal cannula manifolds are used to deliver supplemental oxygen to hospital patients who require respiratory support and to collect carbon dioxide samples from the patients to monitor respiration. The oral/nasal manifold is configured to be in close proximity to the oral cavity and also inserted into the nasal cavity of the patient. The patient's exhaled breath is drawn through the manifold passages to a gas analyzer to be analyzed. The results of this analysis provides an indication of respiratory adequacy.

The accuracy of this analysis of exhaled gases depends on the ability of a sampling system to optimally move a gas sample from the patient to the gas analyzer while maintaining a smooth, laminar flow of gases, such that there are as few alterations to the waveform and response time of the concentration of the gases as possible. The waveform of the concentration of the gas is critical for accurate analysis. As the gas mixtures travel from the patient to the gas analyzer, the concentration of the gases can be effected by mixing of the component gases, which reduces the accuracy of the analysis of the sample by the gas analyzer, and reduces the amount of information obtained from the analysis.

As is pointed out in U.S. Pat. No. 6,422,240, prior art oral/nasal cannulas have caused significant alterations to these important features of the internal structure of the stream of exhaled gases. For example, alterations arise as a result of attempt to combine the delivery of oxygen with the sampling of the exhaled breath of the patient. As another example, prior art oral/nasal cannulas have cannula passages which include connected adjacent or ancillary void volumes (space which is not part of the designated pathway for the flow of gases), and in addition, the cannula passages have curved sections which provide restriction to flow of the respired gases and therefore provide different flow rates in connected cannula passages. Accordingly, the waveform of the concentration of the gas is altered and accurate analysis is not provided. There is accordingly a need to provide an oral/nasal manifold which provides optimal sampling of the subjects exhaled gases for analysis in order to provide an optimal waveform from the analyzer.

The deficiency in these prior art designs is the undesirable diminished fidelity resulting from gas sampling flow dynamics. Specifically, the amount of curvature in the cannula passages and the amount of dead or void space gases, which have limited or no carbon dioxide content, that is analyzed along with the actual ventilatory gases, results in a diluted sample which produces a lesser quality or low fidelity signal generation.

In fact, the flow path created by the drafting effect in the cannula passages is more prominent on the void or dead space gases. This facilitates the production of diluted end title carbon dioxide data and provides a lesser fidelity capnographic waveform and the curvatures and ancillary void volumes in the cannula passages prevent optimal cancellation of signal degradation caused by lack of expiration at the opposite site. In other words, the nasal and oral samples are somewhat in parallel and not in opposition with each other thereby providing degraded sampling quality.

Another deficiency in the prior art designs is that the oral collectors are inefficient and ineffective and an excessive amount of external gases are mixed with the orally exhaled gases thereby providing inaccurate readings.

SUMMARY OF THE INVENTION

The oral/nasal manifold of the present invention is provided for sampling exhaled breath of a patient and to thereby provide an optimal sampling of the subject's exhaled gases for analysis. The oral/nasal manifold is provided with a main body portion having formed therein a suction port which is dimensioned and adapted to be connected with a collection conduit to a suction device for capnographic analysis. A nasal prong protrudes from the main body portion and is positioned for insertion into a nostril of the subject to collect nasally exhaled breath of the subject. The nasal prong is provided with a cannula passage in fluid flow communication with a conduit passage of the suction port. An imbedded oral conduit also passes through the main body portion in an opposite direction and is provided also with a passage with an elongate lateral opening exposing an elongate channel positioned for placement near the oral cavity or mouth of the subject to collect orally exhaled breath of the subject. This oral conduit passage is also in fluid flow communication with the conduit passage of the suction port.

The manifold passage of the nasal prong is connected to and aligned in the same plane as the straight conduit passage of the oral sampling port whereby the opposed nasal and oral passages are connected with the conduit passage of the suction port without any adjacent connected dead or void volumes and without any curvatures in the respective passages. Accordingly, the pressure of the exhaled nasal and oral gases of the subject directly oppose each other in the aligned passages to provide optimal sampling of the subject's exhaled gases for analysis. This opposing effect provides cancellation of the influences of the oral and nasal sites, one against the other, without the inclusion of flow restrictions due to the influence of adjacent or ancillary included void volumes or dead spaces in the manifold passages.

In order to enhance performance of the oral collection portal, a deflector concentrator plate is provided whereby it surrounds the elongate oral opening and exposed elongate channel of the oral conduit prong. This provides an significantly greater surface area from which to obtain a more accurate representative carbon dioxide sample from the oral collection portal.

The oral prong is provided with or includes at least one additional oral prong that is connected to and extends laterally from the main oral prong. These laterally extending prongs are also provided with elongate lateral openings that expose an elongate channel in the deflector/concentrator plate that communicates and connects to the oral passage and channel of the main oral prong. The multiple splayed channels in the deflector/concentrator plate accordingly provide more assured collection of breath exhalation from the patient with minimal intermixing of ambient gases.

It is further preferable that the main body portion and the collection pathway of the oral/nasal manifold be formed of a flame retardant thermoplastic polymer in order to reduce the hazzard of fire sometimes experienced with the use of supplemental oxygen administration.

BRIEF DESCRIPTION OF THE DRAWINGS

Other objects and advantages appear hereinafter in the following description and claims. The accompanying drawings show, for the purpose of exemplification, without limiting the scope of the invention or appended claims, certain practical embodiments of the present invention wherein:

DETAILED DESCRIPTION OF A PREFERRED EMBODIMENT

Figure 1:
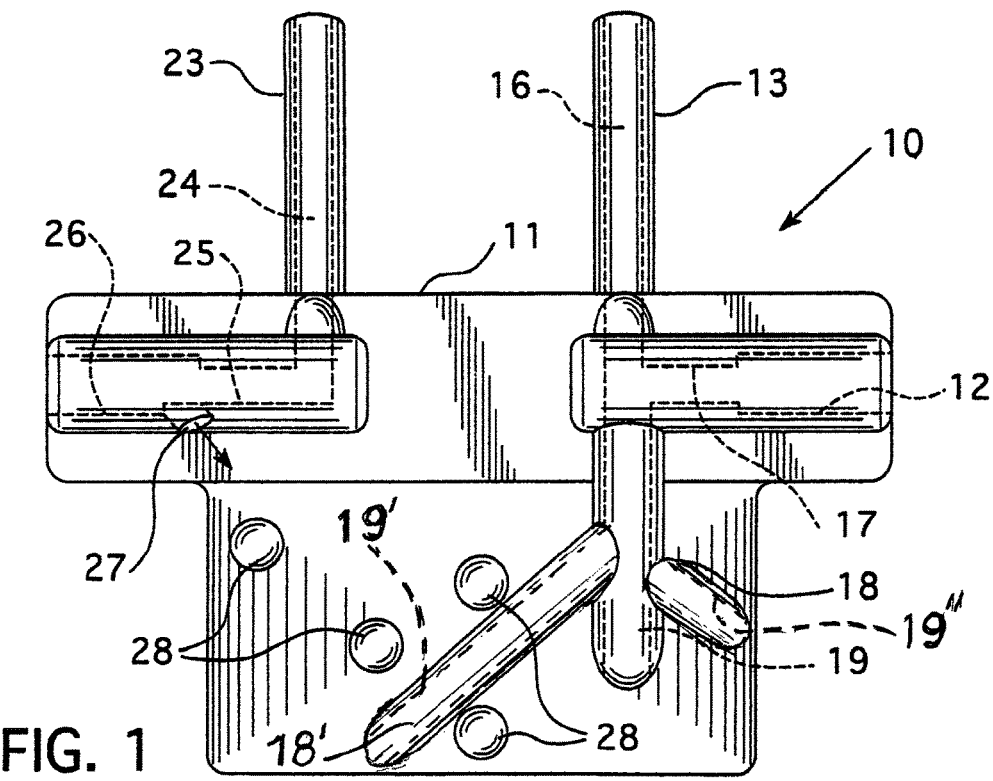
FIG. 1 is a front view of the oral/nasal gas collection manifold of the present invention.

Referring to the drawings, oral/nasal cannula manifold 10 of the present invention is provided for sampling exhaled breath of a subject and includes a main body portion 11 having formed therein a suction port 12 (FIG. 1) which is dimensioned and adapted to be connected with a collection tube (not shown) to a suction device (not shown) for sampling of exhaled breath of the subject known as a capnographic analyzer in the industry for determining the respired $CO_2$ content.

Figure 7:
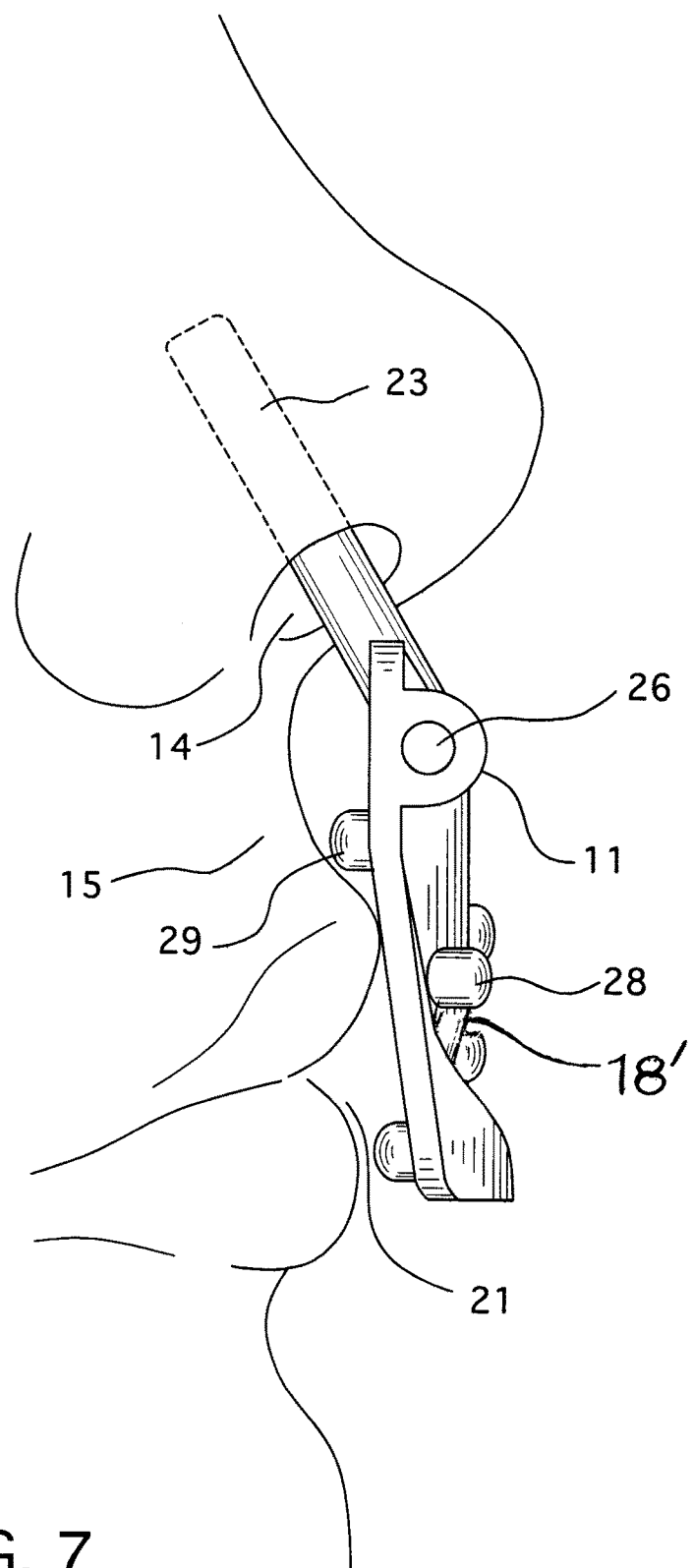
FIG. 7 is a left side view of the oral/nasal gas collection manifold shown in FIG. 1.

A nasal prong 13 protrudes upwardly from main body portion 11 and is positioned for insertion into a nostril (similar to that as shown at 14 in FIG. 7) to collect nasally exhaled breath of the subject 15. Nasal prong 13 is provided with an internal straight passage 16 which is in fluid flow communication with conduit passage 17 of suction port 12.

Oral prong 18 is directed downwardly through the main body portion 11 and is also provided with a conduit passage 19 having an elongate lateral opening 20 for placement near the mouth or oral cavity 21 (FIG. 7) of subject 15 to collect orally exhaled breath of subject 15. This conduit passage 19 provides an open elongate channel that is also in fluid flow communication with the cannula passage 17 of suction port 12.

The straight conduit passage 16 of nasal prong 13 is connected to and aligned in the same plane as the conduit passage 19 of oral prong 18 whereby the opposed nasal and oral passages 16 and 19 are connected with conduit passage 17 of suction port 12 without any adjacent connected void volumes or dead spaces in any of these respective passages. In view of this, the pressure of the exhaled nasal and oral gases of subject 15 directly oppose each other in the straight aligned conduit passages 16 and 19 to thereby provide optimal sampling of the subject's exhaled gases for analysis.

To enhance this feature of optimal sampling, the conduit passage 17 of suction port 12 is preferably connected at a right angle as shown in FIG. 1 to the straight aligned conduit passages 16 and 19, and is connected centrally between their distal ends. Preferably also the internal volumes of the opposed aligned inlets of conduit passages 16 and 19 are equal and the internal diameters of these opposed aligned conduit passages are also equal. This provides for effective reciprocal cancellation at the site of less expiratory force.

Main body portion 11 also includes a curved deflector/concentrator plate 22 which surrounds the elongate opening 20 of the elongate channel of oral prong 18 in order to deflect and concentrate orally exhaled breath from the subject into the elongate channel of oral passage 19 and thereby provide a heavier concentration of the orally exhaled breath with limited dilution with ambient gases.

Oral prong 18 includes two additional oral prongs 18' and 18" which extend laterally in a splayed configuration from nasal prong 19, and are provided with elongate lateral openings 20' and 20" respectively in deflector/concentrator plate 22 which provide corresponding elongate channels in the their internal oral passages 19' and 19", which connect to and communicate with a channel of elongate passage 19. This configuration further enhances a heavier concentration of the orally exhaled breath with minimal dilution with ambient gases.

Main body portion 11, including all integral collection conduit elements thereof, is preferably manufactured of a flame retardant thermoplastic polymer in order to provide an oral/nasal gas collection/delivery manifold which will not propagate or support combustion even in the presence of increased concentrations of oxygen, thereby limiting possible hazardous injuries to the subject.

As viewed in FIG. 1, the left side of the body portion 11 is provided with an oxygen delivery prong 23 which is provided therein with an oxygen delivery passage 24, which in turn is connected to the horizontally oriented oxygen delivery passage 25. Oxygen delivery passage 25 is in turn connected to oxygen supply port 26 which is dimensioned and adapted to receive the terminal end of a flexible oxygen supply tube for supplying oxygen under pressure from a source (not shown).

Figure 2:
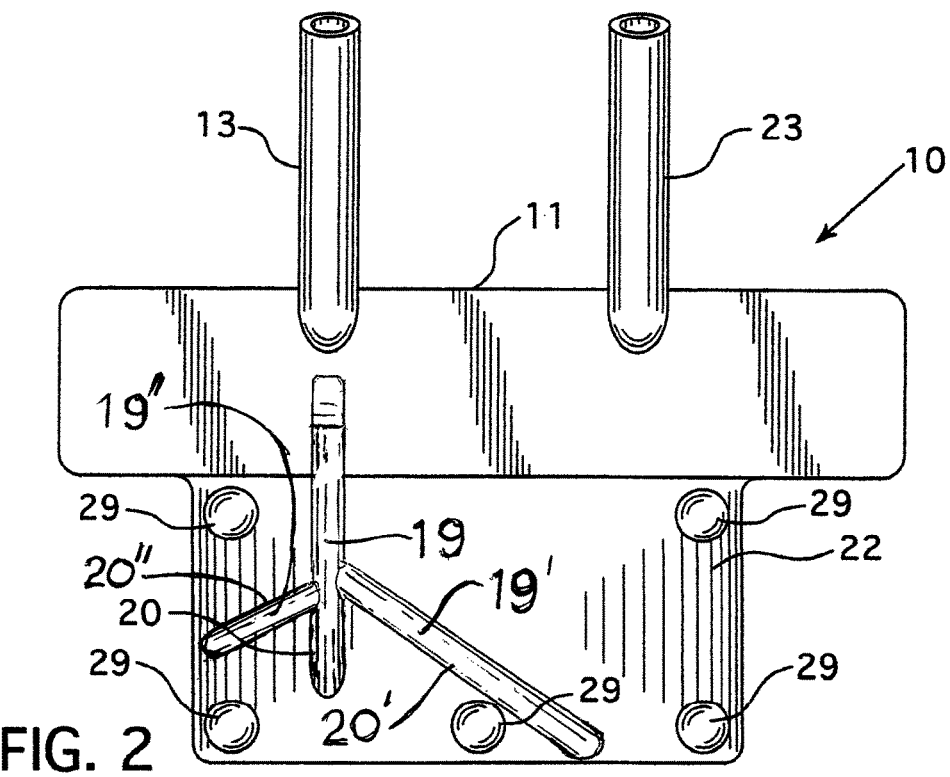
FIG. 2 is a back view of the oral/nasal gas collection manifold shown in FIG. 1.
Figure 3:
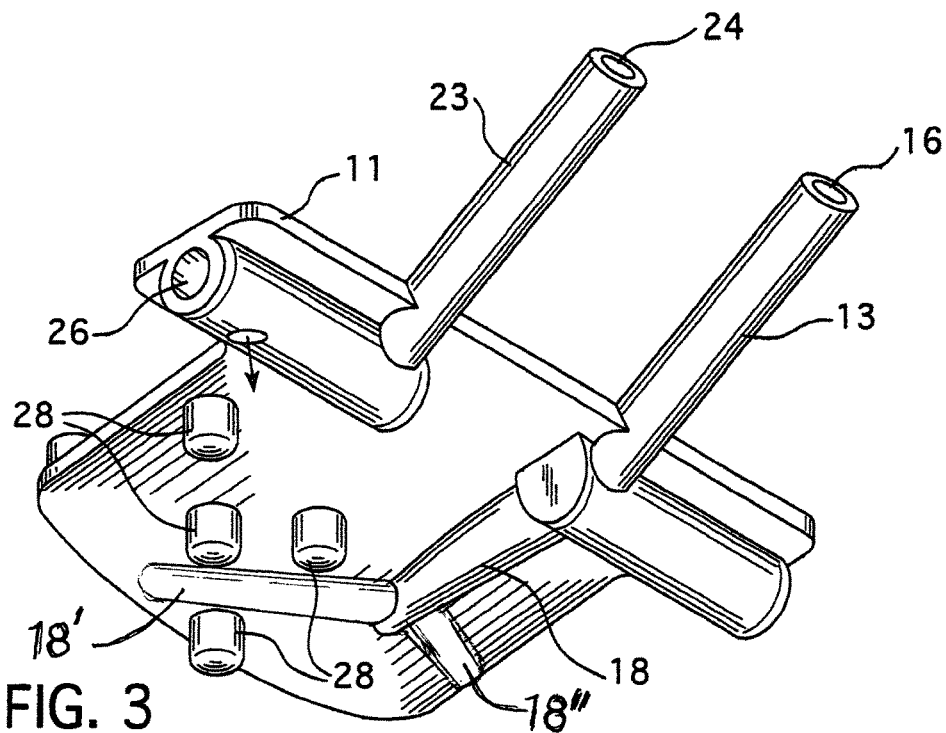
FIG. 3 is a perspective front view of the oral/nasal gas collection manifold shown in FIG. 1.
Figure 4:
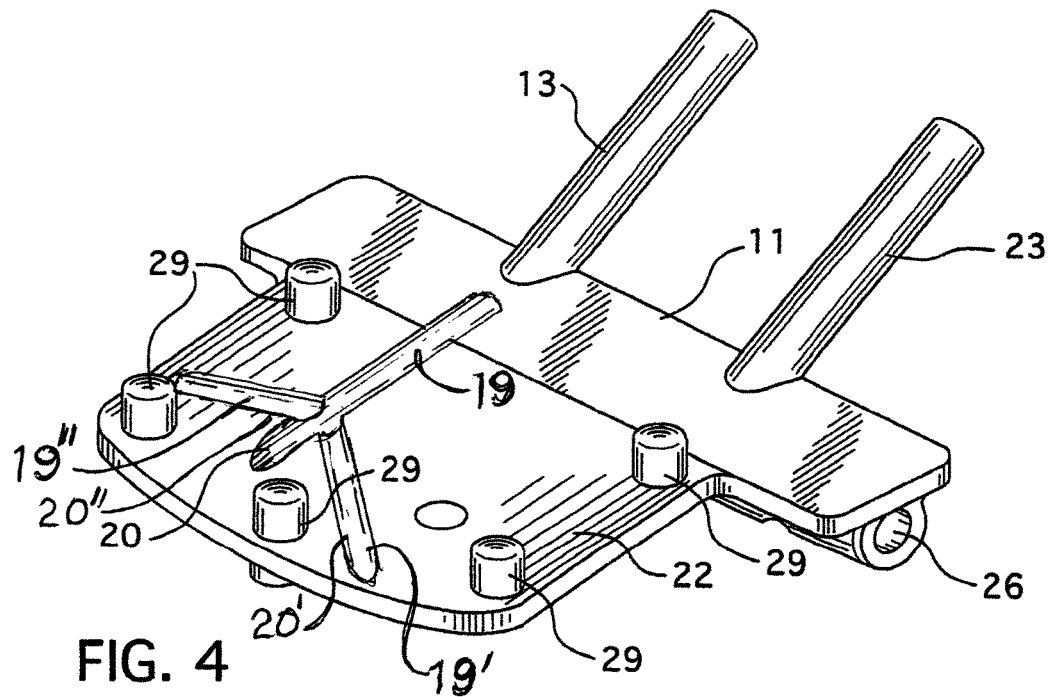
FIG. 4 is a perspective back view of the oral/nasal gas collection manifold of FIG. 1.
Figure 5:
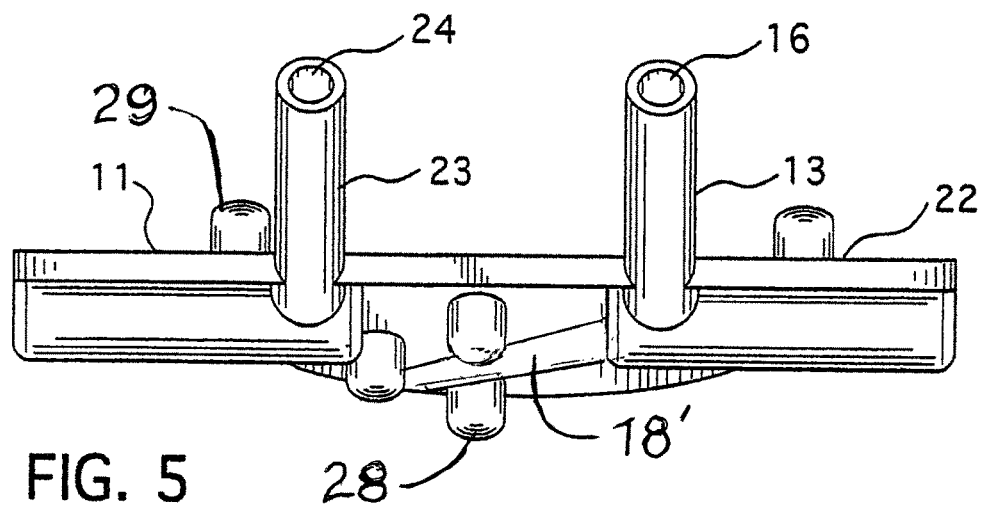
FIG. 5 is a top view of the oral/nasal gas collection manifold shown in FIG. 1.
Figure 6:
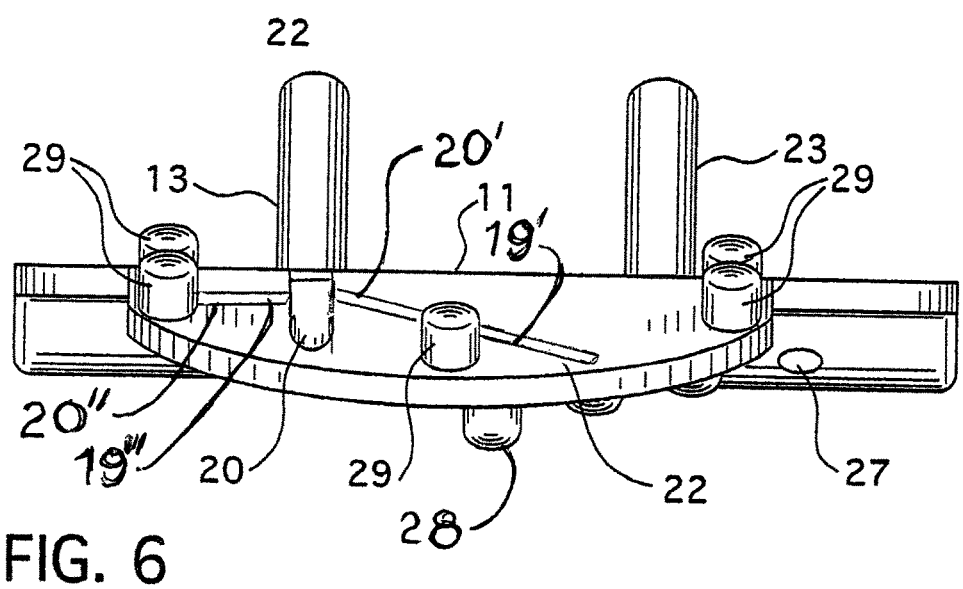
FIG. 6 is a bottom view of the oral/nasal gas collection manifold shown in FIG. 1.

Oxygen supply passage 25 also exits to oral oxygen supply port 27 which supplies a stream of oxygen directed downwardly over the surface of the deflector/concentrator plate towards the mouth of the subject for oral inhalation. However, port 27 is positioned from the outer surface of the deflector plate 22 as indicated in FIGS. 1 and 2, while distal port 20 of passage 19 is situated on the underside of the plate 22 so that the oxygen supply ejected from port 27 does not interfere with or dilute the expired $CO_2$ oral samples entering distal opening 20. In fact, it will be realized that all of the oxygen supply is removed as far as possible away from the exterior distal ports of nasal prong 13 and oral conduit passage 19 so as to prevent any interference between the oxygen supply and the expired or exhaled breath being sampled.

On the outer surface of deflector/concentrator plate 22, a series of raised dispersion protrusions 28 act to create a more uniform envelope of increased oxygen concentration about the mouth and nose.

Raised concentration protrusions 29 on the underside of plate 22 serve to localize a more representative concentration of orally expired carbon dioxide for optimal gas analysis and interpretation.

I claim:

1. An oral/nasal gas sampling and oxygen delivery manifold for sampling exhaled breath of a subject and delivering supplemental oxygen, comprising:

a main body portion having formed therein a suction port which is dimensioned and adapted to be connected with a collection tube to a suction device for sampling of exhaled breath of said subject;

a nasal prong protruding from said main body portion and positioned for insertion into a nostril of said subject to collect nasally exhaled breath of said subject, and having a nasal passage in fluid flow communication with a conduit passage of said suction port; and an oral prong elongate open channel surrounded by a deflector/concentrator plate protruding from said main body portion and having a conduit oral passage with an elongate lateral opening providing said elongate open channel in said oral passage positioned for placement near an oral cavity of said subject to collect orally exhaled breath of said subject, and in fluid flow communication with the conduit passage of said suction port;

the nasal passage of said nasal prong connected to and aligned in the same plane as the oral passage of said oral prong whereby the opposed nasal and oral passages are connected with said conduit passage of said suction port, and the pressure of the exhaled nasal and oral gases of said subject directly oppose each other in said aligned passages to provide optimal sampling of the said subjects exhaled gases for analysis;

said elongate open channel exposing the junction of fluid flow communication between said elongate open channel and said conduit passage of said suction port.

2. The oral/nasal manifold of claim 1, including at least one additional oral prong connected to and extending laterally from said oral prong and having an elongate lateral opening providing an elongate channel in said deflector/concentrator plate connecting to said oral passage.

3. The oral/nasal manifold of claim 1, wherein said main body portion and said prongs are comprised of a flame retardant thermoplastic polymer.

\* \* \* \* \*